US012629534B2

(12) United States Patent
Yaacobi et al.

(10) Patent No.: US 12,629,534 B2
(45) Date of Patent: May 19, 2026

(54) APPARATUS AND METHOD FOR ARRAY POSITIONING

(71) Applicant: NOVOCURE GMBH, Root (CH)

(72) Inventors: Elie Yaacobi, Haifa (IL); Shalom Strauss, Haifa (IL)

(73) Assignee: NOVOCURE GMBH, Baar (CH)

( * ) Notice: Subject to any disclaimer, the term of this patent is extended or adjusted under 35 U.S.C. 154(b) by 271 days.

(21) Appl. No.: 18/490,315

(22) Filed: Oct. 19, 2023

(65) Prior Publication Data

US 2024/0131351 A1 Apr. 25, 2024
US 2024/0226590 A9 Jul. 11, 2024

Related U.S. Application Data

(60) Provisional application No. 63/380,115, filed on Oct. 19, 2022.

(51) Int. Cl.
*A61N 1/40* (2006.01)
*A61B 90/00* (2016.01)
*A61N 1/04* (2006.01)
*G06T 3/06* (2024.01)
*G06T 7/73* (2017.01)

(52) U.S. Cl.
CPC .............. *A61N 1/40* (2013.01); *A61B 90/39* (2016.02); *A61N 1/0476* (2013.01); *G06T 3/06* (2024.01); *G06T 7/73* (2017.01); *A61B 2090/3937* (2016.02); *G06T 2207/10081* (2013.01);
(Continued)

(58) Field of Classification Search
CPC .... A61N 1/40; A61N 1/0476; A61N 1/36002; A61B 90/39; A61B 2090/3937; G06T 3/06; G06T 7/73; G06T 2207/10081; G06T 2207/10088; G06T 2207/30096; G16H 20/40; G16H 30/40; G16H 40/67; G16H 50/50
See application file for complete search history.

(56) References Cited

U.S. PATENT DOCUMENTS

2021/0299439 A1 9/2021 Shamir et al.
2022/0096853 A1 3/2022 Bakalo et al.
(Continued)

FOREIGN PATENT DOCUMENTS

WO WO 2021/069966 4/2021
WO WO-2021097202 A1 * 5/2021 ............. A61B 5/291

OTHER PUBLICATIONS

International Search Report and Written Opinion were mailed on Feb. 5, 2024 by the International Searching Authority for International Application No. PCT/IB2023/060583 filed on Oct. 19, 2023 and published as WO2024084437 (Applicant—Elie Yaacobi) (8 pages).

*Primary Examiner* — Ankit D Tejani
*Assistant Examiner* — Joshua Brendon Solomon
(74) *Attorney, Agent, or Firm* — Ballard Spahr LLP

(57) ABSTRACT

A method includes generating, from an electronic 3-dimensional map indicating placement locations of a plurality of electrode arrays, an electronic 2-dimensional map indicating placement locations of the plurality of electrode arrays relative to each other in 2-dimensional space. The electronic 3-dimensional map is associated with a surface area of at least a portion of a body of a patient. The electronic 3-dimensional map indicating the placement locations of the plurality of electrode arrays can be generated based on at least one medical image.

20 Claims, 8 Drawing Sheets

(52) U.S. Cl.
CPC .............. *G06T 2207/10088* (2013.01); *G06T 2207/30096* (2013.01)

(56) References Cited

U.S. PATENT DOCUMENTS

2022/0369985 A1 * 11/2022 Zabinski ................ A61B 5/304
2024/0061398 A1 * 2/2024 Hershkovich ......... B33Y 50/00

* cited by examiner

APPARATUS AND METHOD FOR ARRAY POSITIONING

CROSS-REFERENCE TO RELATED APPLICATIONS

This application claims priority to and the benefit of the filing date of U.S. Provisional Patent Application No. 63/380,115, filed Oct. 19, 2022, the entirety of which is hereby incorporated by reference herein.

FIELD

This application relates to systems and methods for positioning electrode arrays.

BACKGROUND

Tumor Treating Fields (TTFields) therapy is a proven approach for treating tumors using alternating electric fields at frequencies between 50 kHz-1 MHz, more commonly, 100-500 kHz. In current commercial systems, the alternating electric fields are induced by electrode assemblies (e.g., arrays of capacitively coupled electrodes, also called transducer arrays or electrode arrays) placed on opposite sides of a target region of the subject's body. When an AC voltage is applied between opposing electrode arrays, an AC current is coupled through the electrode arrays and into the subject's body.

Proper positioning of electrode arrays relative to each other and a target region (e.g., a tumor) can affect performance of treatment. However, proper placement can be difficult, particularly when the subject is placing the electrode arrays on himself/herself. Thus, this difficulty can diminish the independence of the subject, requiring the subject to have another person (helper) position the electrode arrays. Accordingly, a way to assist a subject with properly positioning one or more electrode arrays is desirable.

SUMMARY

TTFields are approved for the treatment of glioblastoma multiforme (GBM), and may be delivered, for example, via the OPTUNE® system (Novocure Limited, St. Helier, Jersey), which includes transducer arrays placed on the patient's shaved head. More recently, TTFields therapy has been approved as a combination therapy with chemotherapy for malignant pleural mesothelioma (MPM), and may find use in treating tumors in other parts of the body. For applications targeting tumors in the torso, larger electrode arrays than currently used with the OPTUNE® system may be beneficial.

Disclosed herein, in one aspect, a method includes generating, from an electronic 3-dimensional map indicating placement locations of a plurality of electrode arrays, an electronic 2-dimensional map indicating placement locations of the plurality of electrode arrays relative to each other in 2-dimensional space. The electronic 3-dimensional map is associated with a surface area of at least a portion of a body of a patient. The apparatuses and methods described herein are applicable to facilitating the positioning of one or more electrode array on any part of the body, and not just the head.

In another aspect, a system includes at least one processor and memory in communication with the at least one processor. The memory comprises instructions that, when executed by the at least one processor, cause the at least one processor to generate, from an electronic 3-dimensional map indicating placement locations of a plurality of electrode arrays, an electronic 2-dimensional map indicating placement locations of the plurality of electrode arrays relative to each other in 2-dimensional space. The electronic 3-dimensional map is associated with a surface area of at least a portion of a body of a patient.

In another aspect, an electrode placement map includes a 2-dimensional substrate and visible markings associated with the 2-dimensional substrate. The visible markings are indicative of placement locations of a plurality of electrode arrays relative to each other in 2-dimensional space. The placement locations of the plurality of electrode arrays relative to each other in 2-dimensional space translates to optimized positions of the plurality of electrode arrays for delivering tumor-treating fields when the plurality of electrode arrays are placed on a patient in 3-dimensional space.

In another aspect, a method of using the electrode placement map includes arranging a plurality of electrode arrays onto the electrode placement map, the plurality of electrode arrays comprising at least a first electrode array and a second electrode array. The first and second electrode arrays can be coupled together with a first linkage.

In another aspect, an assembly includes first and second electrode arrays that are spaced and oriented relative to each other according to a 2-dimensional electrode placement map. A first linkage can couple the first and second electrode arrays together.

Figure 1:
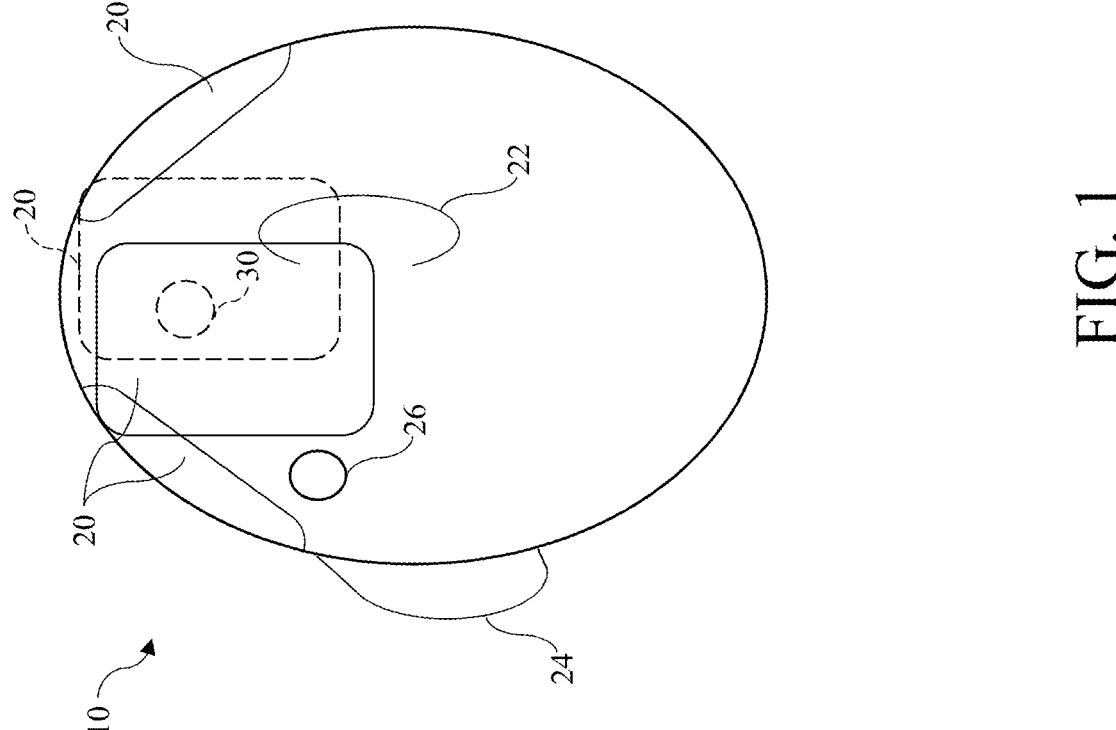
FIG. 1 is a schematic view of an electronic 3-dimensional map as disclosed herein.

Various embodiments are described in detail below with reference to the accompanying drawings, wherein like reference numerals represent like elements, and wherein descriptions of like elements may not be repeated for every embodiment, but may be considered to be the same if previously described herein.

DESCRIPTION OF THE PREFERRED EMBODIMENTS

This application relates to positioning of electrode arrays that may be used, e.g., for delivering TTFields to a subject's body and treating one or more cancers or tumors located in the subject's body.

The present invention can be understood more readily by reference to the following detailed description, examples, drawings, and claims, and their previous and following description. However, it is to be understood that this invention is not limited to the specific apparatuses, devices, systems, and/or methods disclosed unless otherwise specified, and as such, of course, can vary.

Headings are provided for convenience only and are not to be construed to limit the invention in any manner. Embodiments illustrated under any heading or in any portion of the disclosure may be combined with embodiments illustrated under the same or any other heading or other portion of the disclosure.

Any combination of the elements described herein in all possible variations thereof is encompassed by the invention unless otherwise indicated herein or otherwise clearly contradicted by context.

As used in the specification and the appended claims, the singular forms "a," "an," and "the" include plural referents unless the context clearly dictates otherwise.

As used herein, a "fiducial" can be understood as referring to an object in the field of view of an imaging system that appears in the image produced and that can be used as a point of reference or a measure. Optionally, a "fiducial" can be an anatomical feature of a body of a patient.

Methods for Providing Maps

Figure 2:
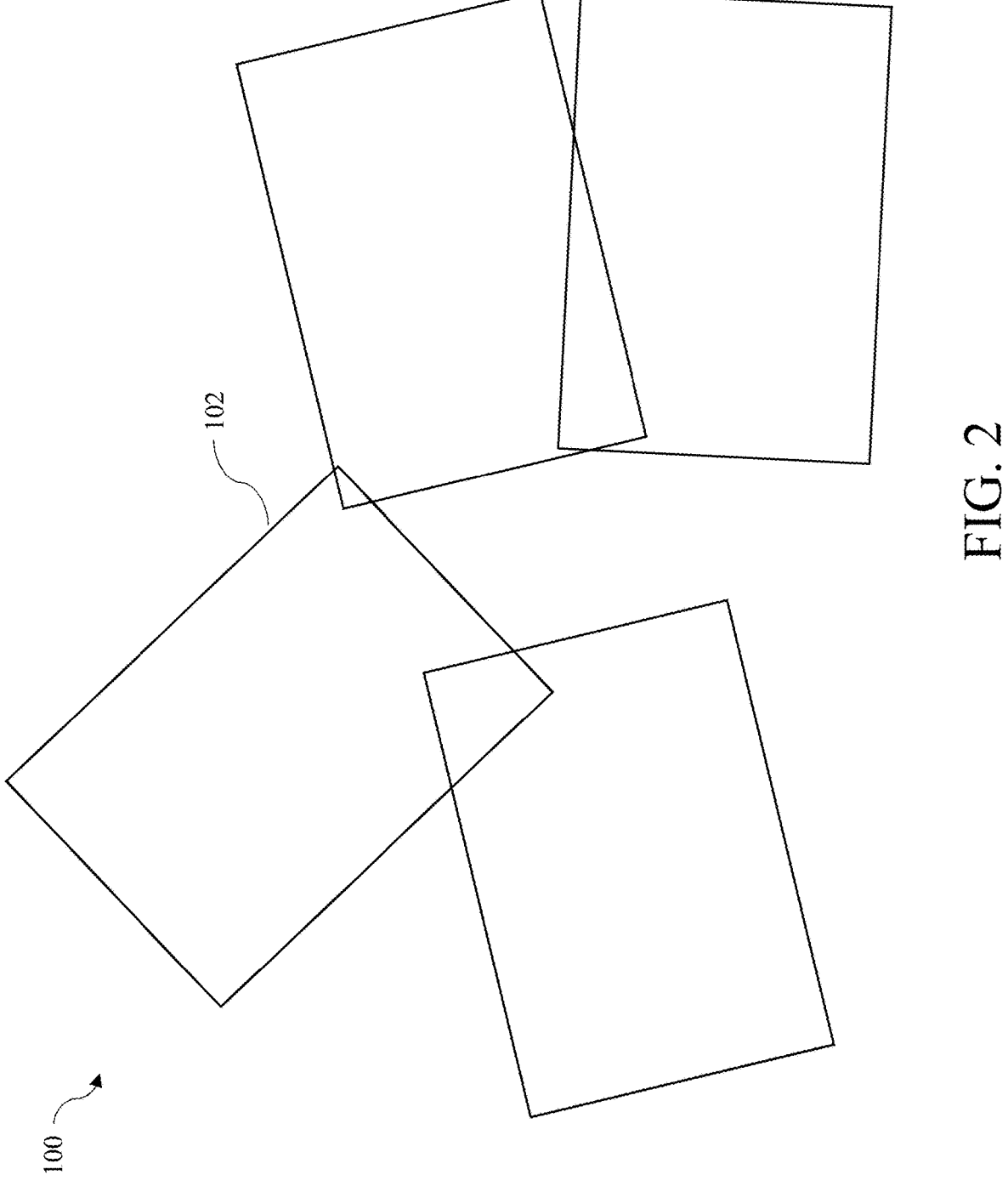
FIG. 2 is a schematic view of an exemplary electronic 2-dimensional map based on the electronic 3-dimensional map of FIG. 1.

Disclosed herein, and with reference to FIGS. 1 and 2, is a method for providing a map for indicating placement locations for a plurality of electrode arrays relative to each other in 2-dimensional space. The method can comprise generating, from an electronic 3-dimensional map 10 (FIG. 1) indicating 3-dimensional placement locations 20 of a plurality of electrode arrays 302 (FIG. 4), an electronic 2-dimensional map 100 indicating 2-dimensional placement locations 102 of the plurality of electrode arrays relative to each other in 2-dimensional space (FIG. 2). In various aspects, the electronic 2-dimensional map 100 can be, or can be convertible to, an image file. The electronic 3-dimensional map can be associated with a surface area of at least a portion of a body of a patient. For example, in some aspects, the portion of the body of the patient can include at least a portion of the head of the patient.

In some aspects, the electronic 2-dimensional map 100 can comprise a plurality of points on a 3-dimensional surface translated to a 2-dimensional surface with the points on the 2-dimensional surface retaining relative spacing therebetween as measured moving along the 3-dimensional surface. For example, in some aspects, the electronic 2-dimensional map 100 can comprise areas of the electronic 3-dimensional map 10 flattened out into 2-dimensional space. Areas of the electronic 3-dimensional map 10 between the placement locations 20 of the plurality of electrode arrays can be extended (e.g., stretched) to maintain linear distances between portions of opposed electrode arrays (e.g., between centroids of the opposed electrode arrays).

Figure 3:
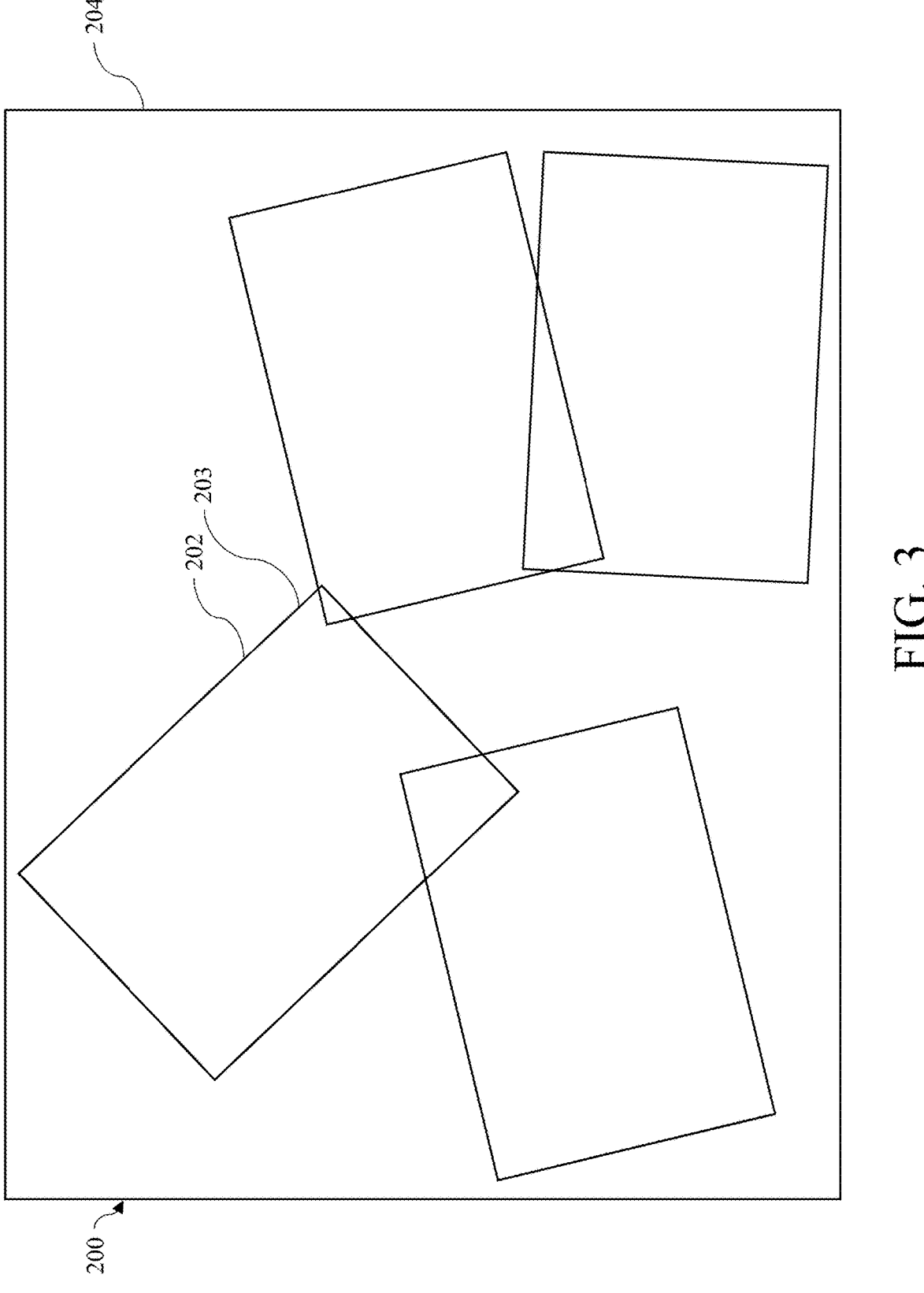
FIG. 3 is a top plan view of an exemplary electrode placement map based on the electronic 2-dimensional map of FIG. 2.
Figure 4:
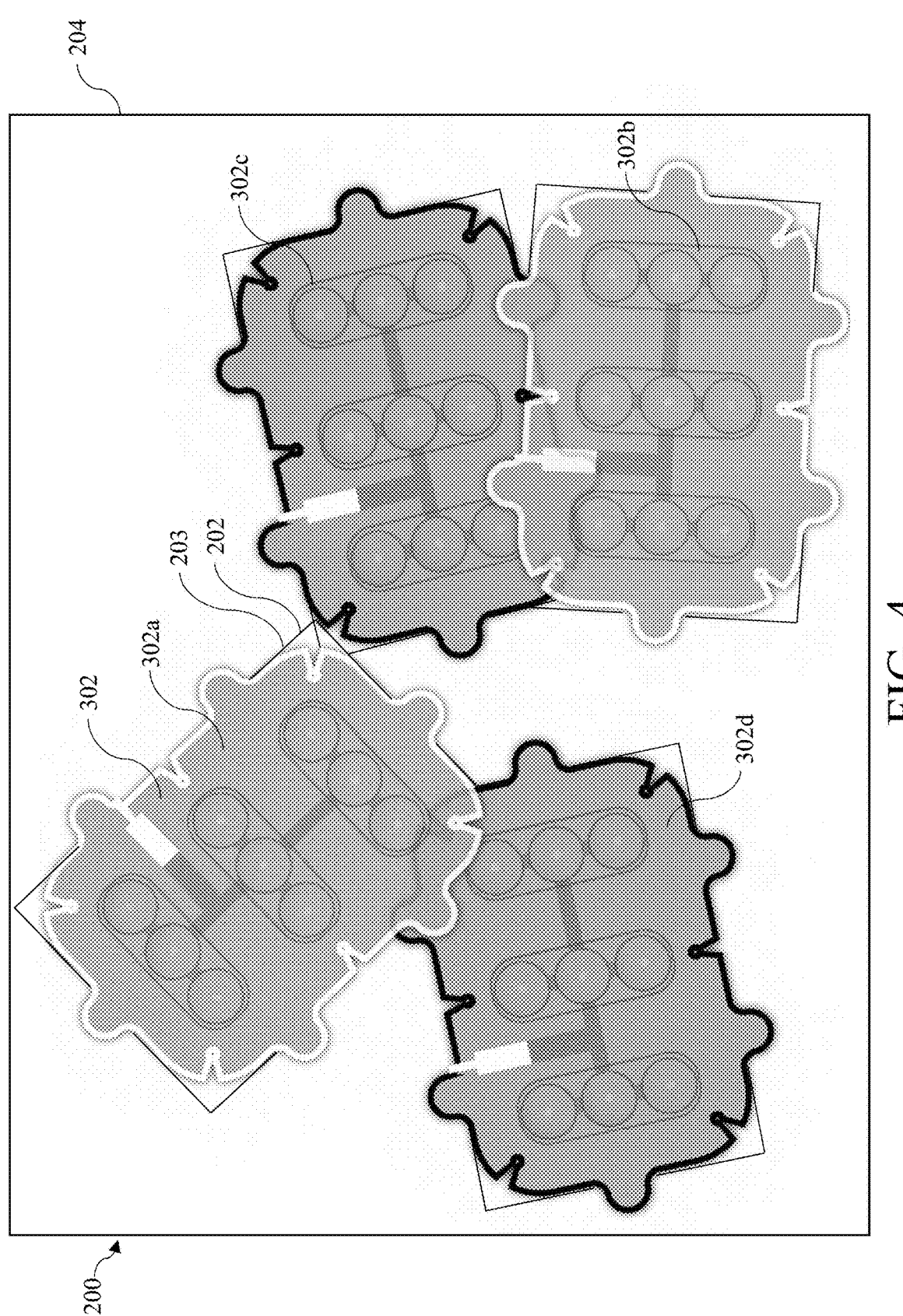
FIG. 4 is a top plan view of a plurality of electrode arrays arranged on the electronic 2-dimensional electrode placement map of FIG. 3.

In some aspects, the placement locations 102 of the plurality of electrode arrays provided on the electronic 2-dimensional map 100 can comprise indications of at least a portion of a perimeter of each electrode array of the plurality of electrode arrays. For example, as illustrated, the electronic 2-dimensional map 100 (or the electrode placement map 200) can comprise rectangles (or 2-dimensional placement locations 102 or 202, FIGS. 2-3) that generally correspond to portions of the outer perimeter of the electrode arrays 302 (FIG. 4). Optionally, as shown in FIGS. 2-4, each of the placement locations 102 of the electronic 2-dimensional map 100 (FIG. 2) and/or the placement locations 202 of the electrode placement map 200 (FIGS. 3-4) and the electrode arrays 302 (FIG. 4) can have corresponding edges that can be at least partially aligned with each other. For example, the outer perimeter of a rectangle of the electrode placement map 200 can have straight edges, and the outer perimeter of a corresponding electrode array 302 (FIG. 4) can have at least some edge portions that can be aligned or substantially aligned with a straight edge of the rectangle of the map. Optionally, it is contemplated that the electrode array 302 can also include edge portions that are positioned inwardly or outwardly of the rectangle of the map. In other aspects, the electronic 2-dimensional map can comprise geometry that traces the exact outer perimeter (or a portion thereof) of a particular array. In still other aspects, the electronic 2-dimensional map can comprise reference points that can correspond to reference points on the outer perimeter of the electrode arrays, and the corresponding reference points can be aligned to ensure proper positioning.

In some aspects, the electronic 3-dimensional map 10 can further comprise at least one fiducial that provides a reference location from which the plurality of electrode arrays can be positioned. In some optional aspects, the electronic 3-dimensional map 10 can comprise a plurality of fiducials. The fiducial(s) can be, for example, an ear 22, a nose 24, an eye 26, an eyebrow, a mouth, or a visible feature on skin of the patient. The visible feature on the skin of the patient can be, for example, a freckle, mole, scar, birth mark, or other unique identifier for spatially orienting the electrode arrays.

In some aspects, the electronic 3-dimensional map 10 indicating the placement locations 20 of the plurality of electrode arrays can be generated based on at least one medical image. The medical image can comprise data showing a location of a target region 30 (e.g., a tumor) in the body of the patient. For example, the medical image can be a magnetic resonance imaging (MRI) image or a computed tomography (CT) scan image, or a combination thereof. The placement locations 20 of the plurality of electrode arrays can be optimized for positioning relative to the target region 30 for delivering tumor-treating fields. Commercial software exists for optimizing the placement of electrode arrays from such 3-dimensional images obtained by MRI imaging or CT scans, such as, for example, MAXPOINT® software (Novocure Limited, St. Helier, Jersey). In some instances, the optimized locations for the electrode arrays may show portions of the outer perimeter of two or more adjacent arrays overlapping. In cases where the overlap affects only the support bandage area of the arrays, it is generally acceptable to cut a portion of one (or more) array as long as the cutting is restricted to the bandage area and does not include the electrodes or electrical circuitry.

Referring also to FIG. 3, in some aspects, the method can further comprise printing visible markings 203 of placement locations 202 associated with the electronic 2-dimensional map 100 (FIG. 2) onto a 2-dimensional substrate 204 to form an electrode placement map 200 (FIG. 3). For example, the 2-dimensional substrate 204 can comprise paper. In some optional aspects, the visible markings 203 can comprise ink or toner printed on the substrate 204.

Electrode Placement Maps

Referring to FIGS. 3-4, an electrode placement map 200 can comprise a 2-dimensional substrate 204 and visible markings 203 of placement locations 202 associated with the 2-dimensional substrate. The visible markings 203 can be indicative of placement locations of a plurality of electrode arrays 302 relative to each other in 2-dimensional space. The placement locations of the plurality of electrode arrays 302 relative to each other in 2-dimensional space can translate to optimized positions of the plurality of electrode arrays for delivering tumor-treating fields when the plurality of electrode arrays are placed on a patient.

For example, the 2-dimensional substrate 204 can comprise paper. In some optional aspects, the visible markings 203 can comprise ink or toner printed on the 2-dimensional substrate 204.

In some aspects, the visible markings 203 can comprise indications of at least a portion of a perimeter of each electrode array of the plurality of electrode arrays. For example, as illustrated, the visible markings 203 can comprise rectangles that generally correspond to portions of the outer perimeter of the electrode arrays. Optionally, as shown in FIGS. 3-4, the visible markings 203 and the electrode arrays can have corresponding edges that can be at least partially aligned with each other. For example, the visible markings 203 can define rectangles having straight edges, and the outer perimeter of a corresponding electrode array 302 can have at least some edge portions that can be aligned or substantially aligned with a straight edge of a corresponding rectangle of the electrode placement map. Optionally, it is contemplated that the electrode array 302 can also include edge portions that are positioned inwardly or outwardly of a corresponding rectangle of the electrode placement map. In other aspects, the visible markings 203 can comprise geometry that traces the exact outer perimeter (or a portion thereof) of a particular array. For example, in some optional aspects, the indications of at least a portion of a perimeter of each electrode array of the plurality of electrode arrays comprises an outline of at least a portion of the perimeter of each electrode array of the plurality of electrode arrays. In still other aspects, the visible markings 203 can comprise reference points that can correspond to (and can be aligned with) reference points on the outer perimeter of the electrode arrays. For example, reference points corresponding to reference points on the outer perimeter of the electrode arrays can include one or more identified fiducials in such instances that the fiducial(s) can help with relative spacing and orientation of the electrode arrays. Optionally, these reference points can be included in the 2-dimensional electrode placement map 200. In other aspects, the visible markings 203 can comprise crosshairs that can indicate a centroid of an electrode array. More generally, the visible markings 203 can provide indications that a user can reference to provide an indication of a placement location and, optionally, an orientation of an electrode array.

Method of Using Electrode Placement Maps

Referring to FIG. 4, a method of using the electrode placement map 200 can comprise arranging a plurality of electrode arrays 302 onto the electrode placement map 200.

The plurality of electrode arrays 302 can be arranged onto the electrode placement map 200 so that the sizing, placement locations and placement orientations of the electrode arrays 302 correspond to those indicated by the visible markings 203.

Figure 5:
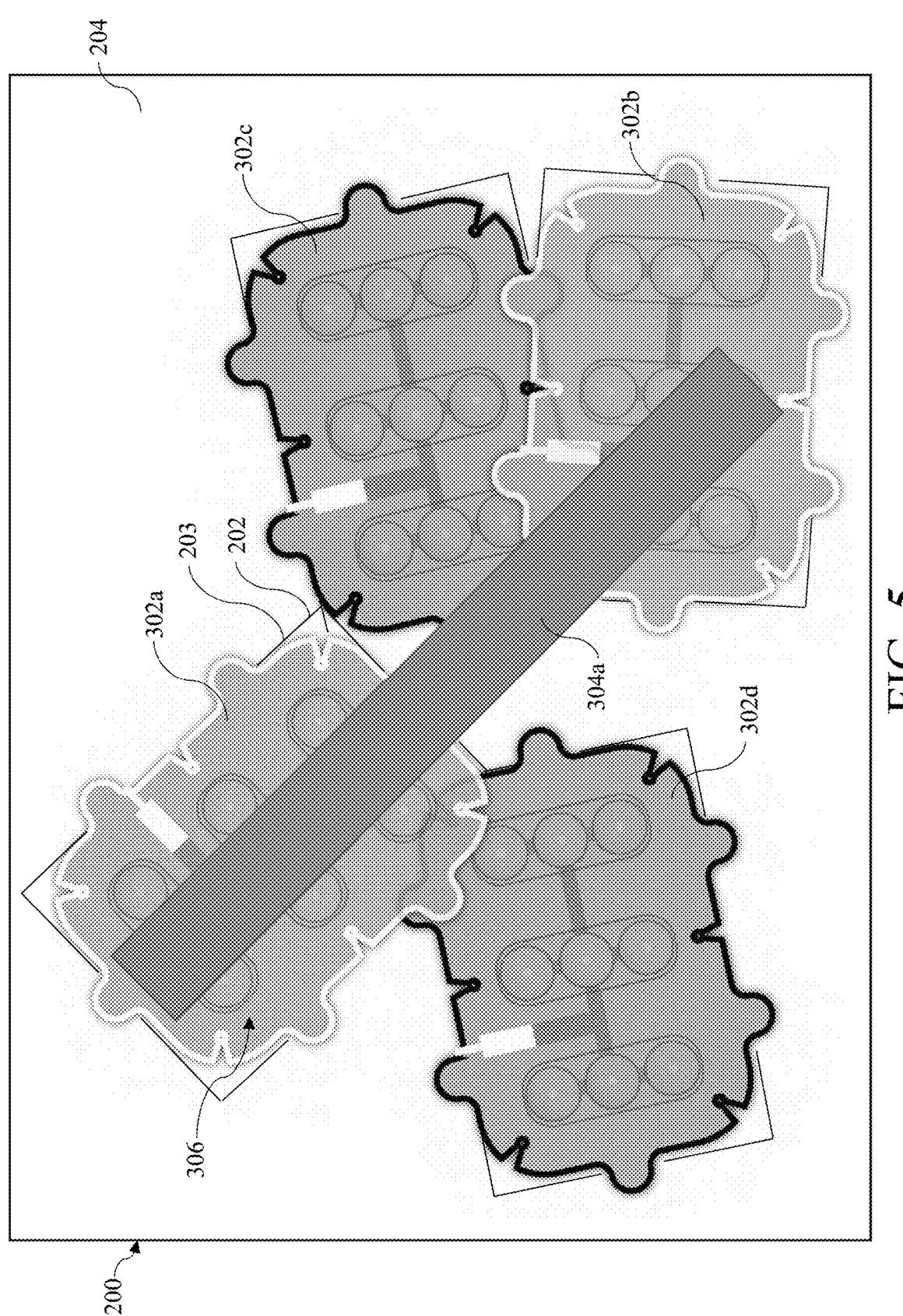
FIG. 5 a top plan view of a plurality of electrode arrays arranged on an electronic 2-dimensional electrode placement map as in FIG. 4, with a first linkage coupling first and second electrode arrays of the plurality of electrode arrays.

The plurality of electrode arrays 302 can comprise at least a first electrode array 302a and a second electrode array 302b. The first and second electrode arrays 302a,b can be coupled together with a first linkage 304a (FIG. 5).

Figure 6:
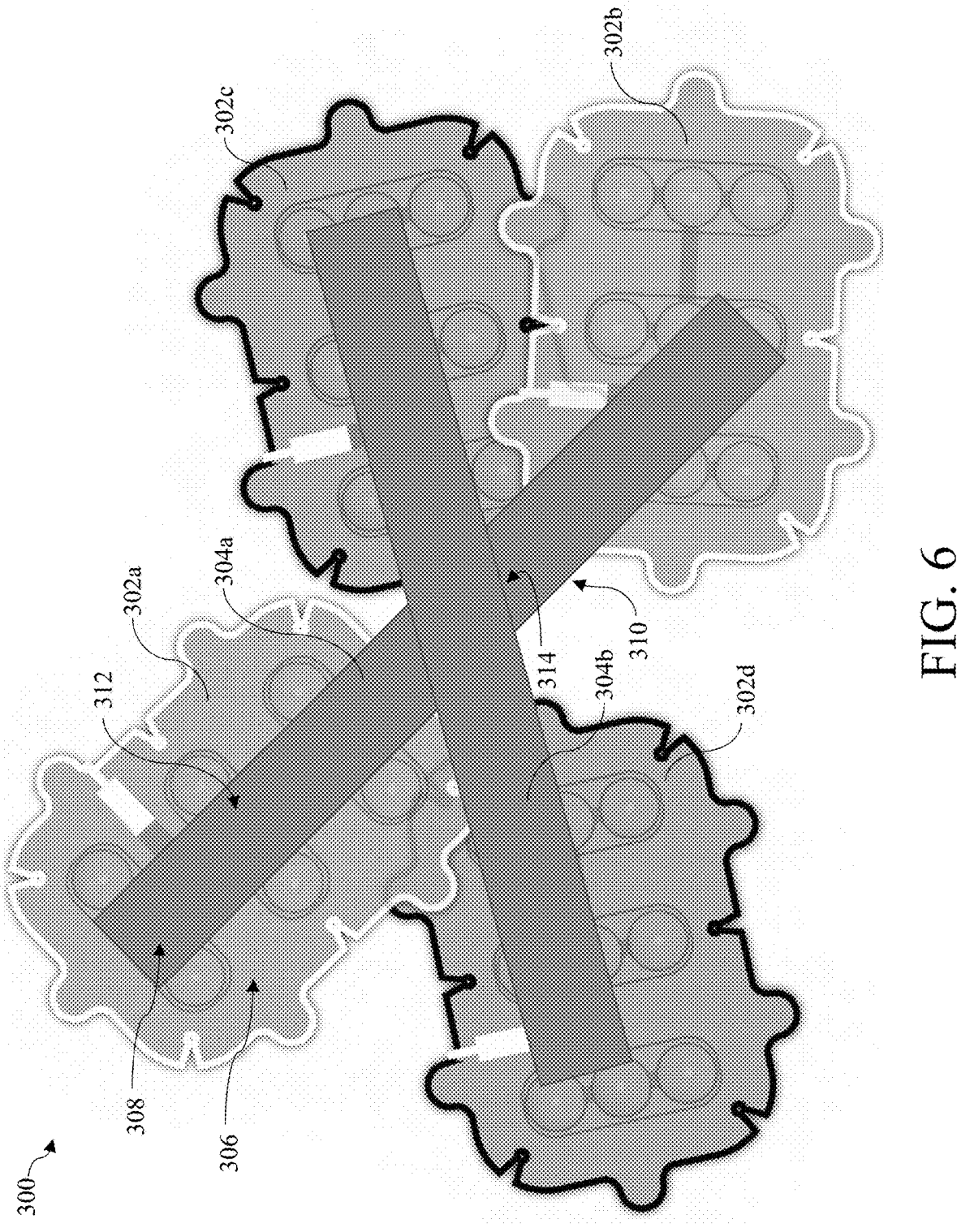
FIG. 6 a top plan view of a plurality of electrode arrays arranged on the electronic 2-dimensional electrode placement map as in FIG. 5, with a second linkage coupling third and fourth electrode arrays of the plurality of electrode arrays.

In some aspects, the plurality of electrode arrays can comprise at least a third electrode array 302c and a fourth electrode array 302d. The third and fourth electrode arrays can be coupled together with a second linkage 304b (FIG. 6). The first and second linkages 304a,b can further be coupled to each other.

The method can further comprise positioning the plurality of electrode arrays on a portion of a body of a patient. For example, the plurality of electrode arrays can be oriented relative to a fiducial (or a plurality of fiducials). The electrode arrays can be adhered to the patient. For example, the electrode arrays can each comprise an adhesive backing and a release liner. The release liner can be removed, and the adhesive backing can be applied directly to the skin of the user. In some aspects, each electrode array 302 can sequentially be adhered to the skin of the user. For example, the release liner of the first electrode array 302a can be removed, and the first electrode array can be adhered to the patient. Subsequently, the release liner of the second electrode array 302b can be removed, and the second electrode array can be adhered to the patient. And similarly for the third electrode array 302c, and the fourth electrode array 302d. Optionally, the method may include, for any given array, leaving the release liner in place on the adhesive side of the array, temporarily positioning that array and checking the positioning by use of additional images prior to removing the release liner and adhering the array to the body.

Once the plurality of electrode arrays are adhered to the patient, the first linkage 304a can be decoupled from the first and second electrode arrays 302a,b. Further, the second linkage 304b can be decoupled from the third and fourth electrode arrays 302c,d. The linkages can be removed in any order: for example, the first linkage 304a can be decoupled from the first and second electrode arrays 302a,b first, and then the second linkage 304b can be decoupled from the first and second electrode arrays 302a,b; or, the second linkage can be decoupled from the first and second electrode arrays 302a,b first, and then the first linkage can be decoupled from the first and second electrode arrays 302a,b. Alternatively, they both can be decoupled from the first and second electrode arrays 302a,b together as one unit, and then decoupled from one another.

The first and/or second linkages 304a,b can comprise elongate bodies that extend between and couple to opposed pairs of electrodes. In various optional aspects, the first and/or second linkages 304a,b can be straps. The first and/or second linkages 304a,b can comprise polymer, leather, paper, cardboard, cloth, or any suitable material. The first and/or second linkages 304a,b can be flexible to permit contouring to the body of the patient.

In some aspects, the first and/or second linkages 304a,b can be inelastic. In other aspects, the first and/or second linkages 304a,b can be resiliently elastic. Generally, it is contemplated that each linkage can provide an indication of relative placement between the electrode arrays to which the linkage is coupled. Accordingly, if the linkage is inelastic, the linkage can be held taut both when being coupled to the electrode arrays and when placing the electrode arrays on the patient, thereby maintaining the distance and orientation between the coupled electrode arrays. If the linkage is elastic, it is contemplated that, both during coupling of the electrode arrays and when placing the electrode arrays on the patient, the linkage can be in a retracted (not stretched) configuration, thereby maintaining the distance and orientation between the coupled electrode arrays.

Further, the first and second linkages 304a,b (e.g., straps) can each have a length and a width transverse to the length. For example, in various optional aspects, the first and/or second linkages 304a,b can be rectangular. It is contemplated that the width can be sufficient that any twist in the linkage can be noticed and corrected. As can be understood, a twist in the linkage (e.g., anything but the linkage lying flat) can correspond to both an angular offset and a linear offset between the coupled electrode arrays. In various aspects, the width of the linkage can be at least 0.5 cm, at least 1 cm, at least 2 cm, at least 3 cm, or at least 4 cm.

In various aspects, the first and second linkages 304a,b can comprise hook and/or loop material (e.g., VELCRO ° hook and/or loop material). For example, it is contemplated that the electrode arrays can have outer surfaces 306 that couple to hook and/or loop material, or the electrode arrays can have outer surfaces 306 that have a hook and/or loop material attached thereto to provide a coupling site for the linkage. In further or alternative aspects, the first and second linkages 304a,b can comprise adhesive (e.g., acrylic adhesive) that couples the respective linkages to the electrode arrays. The adhesive can optionally be a pressure sensitive adhesive.

Accordingly, in some aspects, the first linkage 304a can comprise hook and/or loop material that couples to the outer surfaces 306 of the first and second electrode arrays. Thus, the first linkage 304a can couple to the first electrode array 302a at a first coupling 308. The first coupling 308 can be or can comprise a hook and loop type joint.

An assembly 300 can comprise first and second electrode arrays 302a,b that are spaced and oriented relative to each other according to the 2-dimensional electrode placement map 200. The first linkage 304a can couple the first and second electrode arrays 302a,b together. In some aspects, the first linkage 304a can comprise hook and/or loop material that couples to outer surfaces 306 of the first and second electrode arrays 302a,b. In some aspects, the first linkage 304a can comprise adhesive that couples to outer surfaces 306 of the first and second electrode arrays 302a,b. In some aspects, one or more portions of adhesive tape can couple the first linkage 304a to outer surfaces 306 of the first and second electrode arrays 302a,b.

In some aspects, the third and fourth electrode arrays 302c,d can be spaced and oriented relative to each other and relative to the first and second electrode arrays according to the 2-dimensional electrode placement map 200. The second linkage 304b can couple the third and fourth electrode arrays 302c,d together. The second linkage 304b can extend across and can couple to the first linkage 304a (FIG. 6).

In some aspects, the first linkage 304a has an inner side 310 that is coupled to the first and second electrode arrays 302a,b. The first linkage 304a can further comprise an opposed outer surface 312 that is coupled to an inner surface 314 of the second linkage 304b. In some optional aspects, the outer surface 312 of the first linkage 304a can comprise loop material, and the inner surface 314 of the second linkage 304b can comprise hook material that couples to the loop material of the first linkage 304a. In other aspects, the outer surface 312 of the first linkage 304a comprises hook material, and the inner surface 314 of the second linkage 304b comprises loop material that couples to the hook material of the outer surface 312 of the first linkage. In still other aspects, the first and second straps 304a,b can couple to each other via adhesive.

System for Providing Maps

Figure 7:
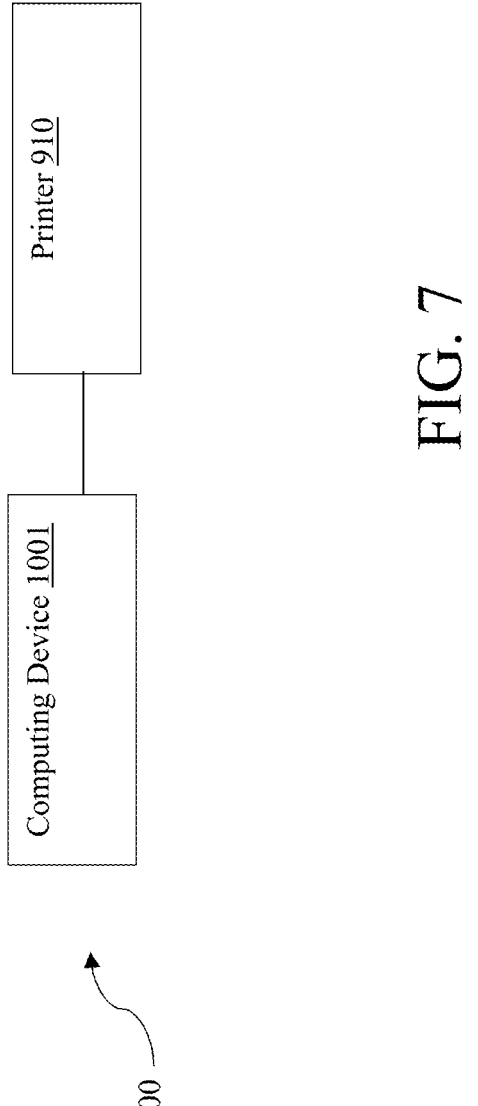
FIG. 7 is a schematic block diagram of a system for providing a map as disclosed herein.

Referring to FIG. 7, in various aspects, a system 900 for providing an electronic 2-dimensional map indicating electrode placement can comprise a computing device 1001 comprising at least one processor and memory in communication with the at least one processor. The memory can comprise instructions that, when executed by the at least one processor, cause the at least one processor to generate, from an electronic 3-dimensional map indicating placement locations of a plurality of electrode arrays, an electronic 2-dimensional map indicating placement locations of the plurality of electrode arrays relative to each other in 2-dimensional space, the electronic 3-dimensional map being associated with a surface area of at least a portion of a body of a patient.

The system 900 can further comprise a printer 910 in communication with the at least one processor. The printer 910 can be configured to print visible markings of placement locations associated with the electronic 2-dimensional map onto a 2-dimensional substrate to form an electrode placement map.

Exemplary Computing Device for Generating 2-dimensional Map

Figure 8:
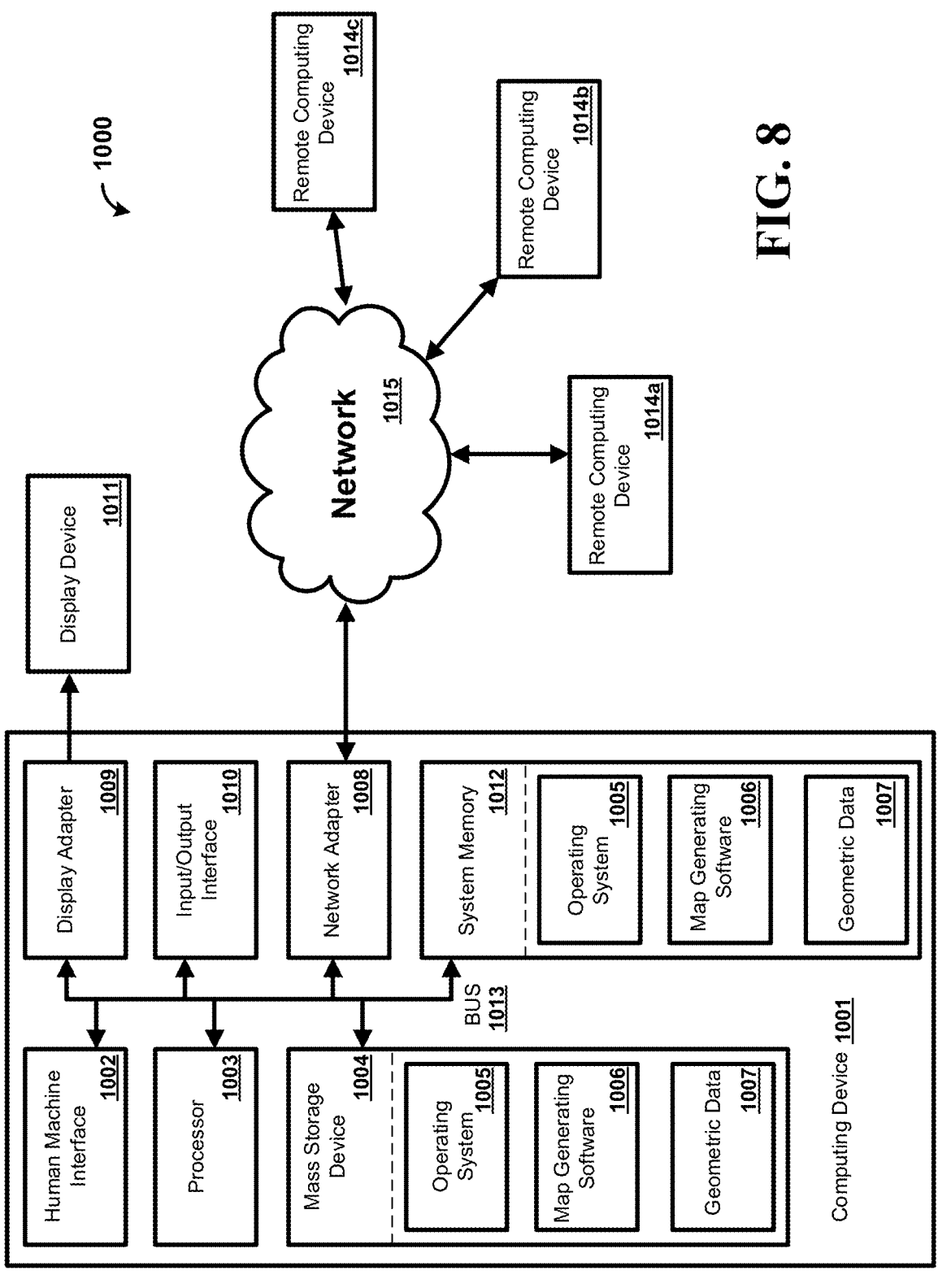
FIG. 8 is a block diagram of an operating environment comprising a computing device of the system of FIG. 7.

FIG. 8 shows an exemplary operating environment 1000 including an exemplary configuration of a computing device 1001 for use with the system 900 (FIG. 7) disclosed herein.

The computing device 1001 may comprise one or more processors 1003, a system memory 1012, and a bus 1013 that couples various components of the computing device 1001 including the one or more processors 1003 to the system memory 1012. In the case of multiple processors 1003, the computing device 1001 may utilize parallel computing.

The bus 1013 may comprise one or more of several possible types of bus structures, such as a memory bus, memory controller, a peripheral bus, an accelerated graphics port, and a processor or local bus using any of a variety of bus architectures.

The computing device 1001 may operate on and/or comprise a variety of computer readable media (e.g., non-transitory). Computer readable media may be any available media that is accessible by the computing device 1001 and comprises, non-transitory, volatile and/or non-volatile media, removable and non-removable media. The system memory 1012 has computer readable media in the form of volatile memory, such as random access memory (RAM), and/or non-volatile memory, such as read only memory (ROM). The system memory 1012 may store data such as geometric data 1007 and/or program modules such as operating system 1005 and map generating software 1006 that are accessible to and/or are operated on by the one or more processors 1003.

The computing device 1001 may also comprise other removable/non-removable, volatile/non-volatile computer storage media. The mass storage device 1004 may provide non-volatile storage of computer code, computer readable instructions, data structures, program modules, and other data for the computing device 1001. The mass storage device 1004 may be a hard disk, a removable magnetic disk, a removable optical disk, magnetic cassettes or other magnetic storage devices, flash memory cards, CD-ROM, digital versatile disks (DVD) or other optical storage, random access memories (RAM), read only memories (ROM), electrically erasable programmable read-only memory (EEPROM), and the like.

Any number of program modules may be stored on the mass storage device 1004. An operating system 1005 and map generating software 1006 may be stored on the mass storage device 1004. One or more of the operating system 1005 and map generating software 1006 (or some combination thereof) may comprise program modules and the map generating software 1006. The geometric data 1007 may also be stored on the mass storage device 1004. The geometric data 1007 may be stored in any of one or more databases known in the art. The databases may be centralized or distributed across multiple locations within the network 1015.

A user may enter commands and information into the computing device 1001 using an input device. Such input devices comprise, but are not limited to, a joystick, a touchscreen display, a keyboard, a pointing device (e.g., a computer mouse, remote control), a microphone, a scanner, a tactile input devices such as gloves, and other body coverings, motion sensor, speech recognition, and the like. These and other input devices may be connected to the one or more processors 1003 using a human machine interface 1002 that is coupled to the bus 1013, but may be connected by other interface and bus structures, such as a parallel port, game port, an IEEE 1394 Port (also known as a Firewire port), a serial port, network adapter 1008, and/or a universal serial bus (USB).

A display device 1011 may also be connected to the bus 1013 using an interface, such as a display adapter 1009. It is contemplated that the computing device 1001 may have more than one display adapter 1009 and the computing device 1001 may have more than one display device 1011. A display device 1011 may be a monitor, an LCD (Liquid Crystal Display), light emitting diode (LED) display, television, smart lens, smart glass, and/or a projector. In addition to the display device 1011, other output peripheral devices may comprise components such as speakers (not shown) and a printer (not shown) which may be connected to the computing device 1001 using Input/Output Interface 1010. Any step and/or result of the methods may be output (or caused to be output) in any form to an output device. Such output may be any form of visual representation, including, but not limited to, textual, graphical, animation, audio, tactile, and the like. The display device 1011 and computing device 1001 may be part of one device, or separate devices.

The computing device 1001 may operate in a networked environment using logical connections to one or more remote computing devices 1014*a,b,c*. A remote computing device 1014*a,b,c* may be a personal computer, computing station (e.g., workstation), portable computer (e.g., laptop, mobile phone, tablet device), smart device (e.g., smartphone, smart watch, activity tracker, smart apparel, smart accessory), security and/or monitoring device, a server, a router, a network computer, a peer device, edge device or other common network node, and so on. The remote computing devices 1014*a,b,c*, can perform respective operations of the system 100. Logical connections between the computing device 1001 and a remote computing device 1014*a, b,c* may be made using a network 1015, such as a local area network (LAN) and/or a general wide area network (WAN), or a Cloud-based network. Such network connections may be through a network adapter 1008. A network adapter 1008 may be implemented in both wired and wireless environments. Such networking environments are conventional and commonplace in dwellings, offices, enterprise-wide computer networks, intranets, and the Internet. It is contemplated that the remote computing devices 1014*a,b,c* can optionally have some or all of the components disclosed as being part of computing device 1001. In various further aspects, it is contemplated that some or all aspects of data processing described herein can be performed via cloud computing on one or more servers or other remote computing devices. Accordingly, at least a portion of the operating environment 1000 can be configured with internet connectivity.

Exemplary Aspects

In view of the described products, systems, and methods and variations thereof, herein below are described certain more particularly described aspects of the invention. These particularly recited aspects should not however be interpreted to have any limiting effect on any different claims containing different or more general teachings described herein, or that the "particular" aspects are somehow limited in some way other than the inherent meanings of the language literally used therein.

Aspect 1: A method comprising:

generating, from an electronic 3-dimensional map indicating placement locations of a plurality of electrode arrays, an electronic 2-dimensional map indicating placement locations of the plurality of electrode arrays relative to each other in 2-dimensional space, wherein the electronic 3-dimensional map is associated with a surface area of at least a portion of a body of a patient.

Aspect 2: The method of aspect 1, wherein the at least a portion of a body of a patient comprises at least a portion of a head of the patient.

Aspect 3: The method of aspect 1, wherein the electronic 2-dimensional map comprises indications of at least a portion of a perimeter of each electrode array of the plurality of electrode arrays.

Aspect 4: The method of aspect 1, wherein the electronic 3-dimensional map further comprises at least one fiducial that provides a reference location from which the plurality of electrode arrays can be positioned.

Aspect 5: The method of aspect 4, wherein the at least one fiducial comprises an ear, a nose, an eye, an eyebrow, a mouth, or a visible feature on skin of the patient.

Aspect 6: The method of aspect 4, or aspect 5, wherein the at least one fiducial comprises a plurality of fiducials.

Aspect 7: The method of any one of aspects 4-6, wherein the at least one fiducial on the electronic 3-dimensional map is marked on the electronic 2-dimensional map.

Aspect 8: The method of any one of the preceding aspects, further comprising generating, based on at least one medical image, the electronic 3-dimensional map indicating the placement locations of the plurality of electrode arrays, wherein the placement locations of the plurality of electrode arrays are optimized for positioning relative to a target region for delivering tumor-treating fields.

Aspect 9: The method of aspect 8, wherein the at least one medical image is an MRI image, or a CT scan, or combination thereof.

Aspect 10: The method of any one of the preceding aspects, wherein the electronic 2-dimensional map comprises a plurality of points on a 3-dimensional surface translated to a 2-dimensional surface with the points on the 2-dimensional surface retaining relative spacing therebetween as measured moving along the 3-dimensional surface.

Aspect 11: The method of any one of the preceding aspects, further comprising printing visible markings associated with the electronic 2-dimensional map onto a 2-dimensional substrate to form a 2-dimensional electrode placement map.

Aspect 12: The method of aspect 11, further comprising:

arranging a plurality of electrode arrays onto the 2-dimensional electrode placement map, the plurality of electrode arrays comprising at least a first electrode array and a second electrode array; and coupling the first and second electrode arrays together with a first linkage.

Aspect 13: The method of aspect 12, wherein the first linkage comprises a strap or strip comprising hook or loop material.

Aspect 14: The method of aspect 12 or aspect 13, wherein the plurality of electrode arrays comprise at least a third electrode array and a fourth electrode array, the method further comprising:

coupling the third and fourth electrode arrays together with a second linkage; and coupling the first and second linkages.

Aspect 15: The method of aspect 13 or aspect 14, further comprising positioning the plurality of electrode arrays on a portion of a body of a patient.

Aspect 16: The method of aspect 15, wherein positioning the plurality of electrode arrays on the portion of the body of the patient comprises orienting the plurality of electrode arrays relative to a fiducial.

Aspect 17: The method of aspect 15 or aspect 16, further comprising:

removing a release liner from each electrode array of the plurality of electrode arrays; and adhering each electrode array of the plurality of electrode arrays to the body.

Aspect 18: The method of any one of aspects 15-17, further comprising decoupling the first linkage from the first and second electrode arrays.

Aspect 19: The method of any one of aspects 15-18, further comprising printing the visible markings onto the 2-dimensional electrode placement map based on an electronic 2-dimensional map.

Aspect 20: The method of any one of aspects 15-19, wherein the first linkage couples to the first electrode array at a first coupling, wherein the first coupling is or comprises a hook and loop type joint.

Aspect 21: An electrode placement map comprising:

a 2-dimensional substrate;

visible markings associated with the 2-dimensional substrate, the visible markings being indicative of placement locations of a plurality of electrode arrays relative to each other in 2-dimensional space, wherein the placement locations of the plurality of electrode arrays relative to each other in 2-dimensional space translates to optimized positions of the plurality of electrode arrays for delivering tumor-treating fields when the plurality of electrode arrays are placed on a patient in 3-dimensional space.

Aspect 22: The electrode placement map of aspect 21, wherein the visible markings comprise ink or toner printed on the 2-dimensional substrate.

Aspect 23: The electrode placement map of aspect 22, wherein the 2-dimensional substrate comprises paper.

Aspect 24: The electrode placement map of any one of aspects 21-23, wherein the visible markings comprise indications of at least a portion of a perimeter of each electrode array of the plurality of electrode arrays.

Aspect 25: The electrode placement map of aspect 24, wherein the indications of at least a portion of a perimeter of each electrode array of the plurality of electrode arrays comprises an outline of at least a portion of the perimeter of each electrode array of the plurality of electrode arrays.

Aspect 26: The electrode placement map of aspect 21, wherein the visible markings comprise indications of at least one fiducial that provides a reference location from which the plurality of electrode arrays can be positioned.

Aspect 27: The electrode placement map of aspect 26, wherein the at least one fiducial comprises an ear, a nose, an eye, an eyebrow, a mouth, or a visible feature on skin of the patient.

Aspect 28: A method of using the electrode placement map of any one of aspects 21-27, the method comprising:

arranging a plurality of electrode arrays onto the electrode placement map, the plurality of electrode arrays comprising at least a first electrode array and a second electrode array; and coupling the first and second electrode arrays together with a first linkage.

Aspect 29: The method of aspect 28, wherein the first linkage comprises a strap or strip comprising hook or loop material.

Aspect 30: The method of aspect 28 or aspect 29, wherein the plurality of electrode arrays comprise at least a third electrode array and a fourth electrode array, the method further comprising:

coupling the third and fourth electrode arrays together with a second linkage; and coupling the first and second linkages.

Aspect 31: The method of any one of aspects 28-30, further comprising positioning the plurality of electrode arrays on a portion of a body of a patient.

Aspect 32: The method of aspect 31, wherein positioning the plurality of electrode arrays on the portion of the body of the patient comprises orienting the plurality of electrode arrays relative to a fiducial.

Aspect 33: The method of aspect 31 or aspect 32, further comprising:

removing a release liner from each electrode array of the plurality of electrode arrays; and adhering each electrode array of the plurality of electrode arrays to the body.

Aspect 34: The method of any one of aspects 31-33, further comprising decoupling the first linkage from the first and second electrode arrays.

Aspect 35: The method of any one of aspects 27-34, further comprising printing the visible markings onto the electrode placement map based on an electronic 2-dimensional map.

Aspect 36: The method of any one of aspects 27-34, wherein the first linkage couples to the first electrode array at a first coupling, wherein the first coupling is or comprises a hook and loop type joint.

Aspect 37: An assembly comprising:

first and second electrode arrays that are spaced and oriented relative to each other according to a 2-dimensional electrode placement map; and a first linkage coupling the first and second electrode arrays together.

Aspect 38: The assembly of aspect 37, wherein the first and second electrode arrays comprise respective outer surfaces, wherein the first linkage comprises hook and/or loop material that couples to outer surfaces of the first and second electrode arrays or couples to hook and/or loop material on the outer surfaces of the first and second electrode arrays.

Aspect 39: The assembly of aspect 38, wherein the first and second electrode arrays comprise respective outer surfaces, and wherein the first linkage comprises adhesive that couples the first linkage to the outer surfaces of the first and second assemblies or one or more portions of adhesive tape couples the first linkage to the outer surfaces of the first and second arrays.

Aspect 40: The assembly of any one of aspects 37-39, further comprising:

third and fourth electrode arrays that are spaced and oriented relative to each other and relative to the first and second electrode arrays according to the 2-dimensional electrode placement map; and a second linkage coupling the third and fourth electrode arrays together, wherein the second linkage extends across and is coupled to the first linkage.

Aspect 41: The assembly of aspect 40, wherein the first linkage has an inner side that is coupled to the first and second electrode arrays, wherein the first linkage comprises an outer surface that is coupled to an inner surface of the second linkage.

Aspect 42: The assembly of aspect 41, wherein the outer surface of the first linkage comprises loop material, and the inner surface of the second linkage comprises hook material, or wherein the outer surface of the first linkage comprises hook material, and the inner surface of the second linkage comprises loop material.

Aspect 43: The assembly of any one of aspects 37-42, wherein the first linkage is inelastic.

Aspect 44: The assembly of any one of aspects 40-43, wherein the second linkage is inelastic.

Aspect 45: A system comprising:

at least one processor; and memory in communication with the at least one processor, wherein the memory comprises instructions that, when executed by the at least one processor, cause the at least one processor to:

generate, from an electronic 3-dimensional map indicating placement locations of a plurality of electrode arrays, an electronic 2-dimensional map indicating placement locations of the plurality of electrode arrays relative to each other in 2-dimensional space, wherein the electronic 3-dimensional map is associated with a surface area of at least a portion of a body of a patient.

Aspect 46: The system of aspect 45, further comprising:

a printer in communication with the at least one processor, wherein the printer is configured to print printing visible markings associated with the electronic 2-dimensional map onto a 2-dimensional substrate to form an electrode placement map.

While the present invention has been disclosed with reference to certain embodiments, numerous modifications, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

What is claimed is:

1. A method comprising:

generating, from an electronic 3-dimensional map indicating placement locations of a plurality of electrode arrays, an electronic 2-dimensional map indicating placement locations of the plurality of electrode arrays relative to each other in 2-dimensional space, wherein the electronic 3-dimensional map is associated with a surface area of at least a portion of a body of a patient; and providing a first linkage that is separate from each electrode array of the plurality of electrode arrays, wherein the first linkage is configured to couple to an outer surface of each of a first electrode array and a second electrode array of the plurality of electrode arrays in an arrangement determined by the electronic 2-dimensional map, following arrangement of the plurality of electrode arrays according to the electronic 2-dimensional map.

2. The method of claim 1, wherein the at least a portion of a body of a patient comprises at least a portion of a head of the patient.

3. The method of claim 1, wherein the electronic 2-dimensional map comprises indications of at least a portion of a perimeter of each electrode array of the plurality of electrode arrays.

4. The method of claim 1, wherein the electronic 3-dimensional map further comprises at least one fiducial that provides a reference location from which the plurality of electrode arrays can be positioned, wherein the at least one fiducial on the electronic 3-dimensional map is marked on the electronic 2-dimensional map.

5. The method of claim 4, wherein the at least one fiducial comprises an ear, a nose, an eye, an eyebrow, a mouth, or a visible feature on skin of the patient.

6. The method of claim 1, further comprising generating, based on at least one medical image, the electronic 3-dimensional map indicating the placement locations of the plurality of electrode arrays, wherein the placement locations of the plurality of electrode arrays are optimized for positioning relative to a target region for delivering tumor-treating fields, wherein the at least one medical image is an MRI image, or a CT scan, or combination thereof.

7. The method of claim 1, wherein the electronic 2-dimensional map comprises a plurality of points on a 3-dimensional surface translated to a 2-dimensional surface with the points on the 2-dimensional surface retaining relative spacing therebetween as measured moving along the 3-dimensional surface.

8. The method of claim 1, further comprising printing visible markings associated with the electronic 2-dimensional map onto a 2-dimensional substrate to form a 2-dimensional electrode placement map.

9. The method of claim 8 further comprising:

arranging a plurality of electrode arrays onto the 2-dimensional electrode placement map, the plurality of electrode arrays comprising at least a first electrode array and a second electrode array; and coupling the first and second electrode arrays together with the first linkage.

10. The method of claim 9, wherein the plurality of electrode arrays comprise at least a third electrode array and a fourth electrode array, the method further comprising:

coupling the third and fourth electrode arrays together with a second linkage; and coupling the first and second linkages.

11. The method of claim 10, wherein either or both of the first linkage and the second linkage comprises a strap or strip comprising hook or loop material.

12. The method of claim 9, further comprising positioning the plurality of electrode arrays on a portion of a body of a patient.

13. The method of claim 12, wherein positioning the plurality of electrode arrays on the portion of the body of the patient comprises orienting the plurality of electrode arrays relative to a fiducial.

14. A kit comprising:

a plurality of electrode arrays, the plurality of electrode arrays comprising a first electrode array and a second electrode array;

an electrode placement map comprising:

a 2-dimensional substrate;

visible markings associated with the 2-dimensional substrate, the visible markings being indicative of placement locations of the plurality of electrode arrays relative to each other in 2-dimensional space, wherein the placement locations of the plurality of electrode arrays relative to each other in 2-dimensional space translates to optimized positions of the plurality of electrode arrays for delivering tumor-treating fields when the plurality of electrode arrays are placed on a patient in 3-dimensional space; and at least one linkage that is separate from each electrode array of the plurality of electrode arrays, wherein a first linkage of the at least one linkage is configured to couple to an outer surface of each of the first electrode array and the second electrode array in an arrangement determined by the electronic 2-dimensional map, following arrangement of the plurality of electrode arrays according to the electronic 2-dimensional map.

15. The kit of claim 14, wherein the visible markings of the electrode placement map comprise ink or toner printed on the 2-dimensional substrate.

16. The kit of claim 15, wherein the 2-dimensional substrate of the electrode placement map comprises paper.

17. The kit of claim 14, wherein the visible markings of the electrode placement map comprise indications of at least a portion of a perimeter of each electrode array of the plurality of electrode arrays.

18. The kit of claim 14, wherein the visible markings of the electrode placement map comprise indications of at least one fiducial that provides a reference location from which the plurality of electrode arrays can be positioned.

19. The kit of claim 14, wherein the plurality of electrode arrays further comprise a third electrode array and a fourth electrode array, wherein the at least one linkage further comprises a second linkage, wherein the second linkage is configured to couple to:

an outer surface of each of the third electrode array and the fourth electrode array of the plurality of electrode arrays in an arrangement determined by the electronic 2-dimensional map, following arrangement of the plurality of electrode arrays according to the electronic 2-dimensional map, and an outer surface of the first linkage.

20. The kit of claim 19, wherein the first linkage has an inner surface and an outer surface, wherein either:

(a) the inner surface of the first linkage comprises hook material that is configured to couple to the outer surface of each of the first and second electrode arrays, wherein the outer surface of the first linkage comprises loop material, and wherein the second linkage comprises hook material that is configured to couple to the outer surface of each of the third and fourth electrode arrays and the loop material of the outer surface of the first linkage; or (b) the inner surface of the first linkage comprises loop material that is configured to couple to the outer surface of each of the first and second electrode arrays, wherein the outer surface of the first linkage comprises hook material, and wherein the second linkage comprises loop material that is configured to couple to the outer surface of each of the third and fourth electrode arrays and the hook material of the outer surface of the first linkage.

* * * * *